(12) United States Patent
Lee

(10) Patent No.: US 10,113,863 B2
(45) Date of Patent: Oct. 30, 2018

(54) VISCOSITY MEASURING METHOD

(71) Applicant: FEMTOBIOMED INC., Seongnam-si, Gyeonggi-do (KR)

(72) Inventor: Sanghyun Lee, Pohang-si (KR)

(73) Assignee: FEMTOBIOMED INC., Seongnam-si, Gyeonggi-do (KR)

( * ) Notice: Subject to any disclaimer, the term of this patent is extended or adjusted under 35 U.S.C. 154(b) by 46 days.

(21) Appl. No.: 15/314,438

(22) PCT Filed: May 15, 2015

(86) PCT No.: PCT/KR2015/004889
§ 371 (c)(1),
(2) Date: Nov. 28, 2016

(87) PCT Pub. No.: WO2015/182907
PCT Pub. Date: Dec. 3, 2015

(65) Prior Publication Data
US 2018/0094916 A1   Apr. 5, 2018

(30) Foreign Application Priority Data
May 28, 2014 (KR) .................. 10-2014-0064405

(51) Int. Cl.
*G06K 9/00* (2006.01)
*G01B 11/24* (2006.01)
(Continued)

(52) U.S. Cl.
CPC .............. *G01B 11/24* (2013.01); *G01N 11/00* (2013.01); *G01N 21/95* (2013.01); *G01N 33/49* (2013.01);
(Continued)

(58) Field of Classification Search
CPC ........ G01B 11/24; G01N 33/49; G01N 11/00; G01N 21/95; G01N 2291/02818; G01N 2011/006; G01F 1/8468
See application file for complete search history.

(56) References Cited

U.S. PATENT DOCUMENTS 7,054,768 B2 *   5/2006   Anderson .............. G01N 13/00
                                                                    382/107
2010/0274504 A1  10/2010  Takahashi
(Continued)

FOREIGN PATENT DOCUMENTS

EP        1950550 A1    7/2008
JP        H02-098651 A  4/1990
(Continued)

OTHER PUBLICATIONS

Extended European Search Report for Application No. 15798839.5, dated Dec. 15, 2017, 6 pages.
(Continued)

*Primary Examiner* — John Strege
(74) *Attorney, Agent, or Firm* — Lewis Roca Rothgerber Christie LLP

(57) ABSTRACT

The present invention relates to a viscosity measuring method. More particularly, the present invention relates to a viscosity measuring method comprising: (i) a step of acquiring an image of a droplet in a static state without vibration; (ii) a step of using a vibrator to vibrate the droplet, and acquiring an image of a dynamic state in which the droplet is maximally extended in a horizontal direction or maximally extended in a vertical direction; (iii) a step of obtaining the static curvature change rate and the dynamic curvature change rate of the interface of the droplet from the images acquired in steps (i) and (ii); and (iv) a step of substituting the ratio of the static curvature change rate to the dynamic curvature change rate of the droplet interface into
(Continued)

an interaction equation compensating for the vibrator, so as to obtain the viscosity of the droplet.

4 Claims, 3 Drawing Sheets

(51) Int. Cl.
*G01N 11/00* (2006.01)
*G01N 33/49* (2006.01)
*G01N 21/95* (2006.01)
*G01F 1/84* (2006.01)

(52) U.S. Cl.
CPC ...... *G01F 1/8468* (2013.01); *G01N 2011/006* (2013.01); *G01N 2291/02818* (2013.01)

(56) References Cited

U.S. PATENT DOCUMENTS

| | | |
|---|---|---|
| 2012/0288926 A1 | 11/2012 | Murayama |
| 2015/0185131 A1* | 7/2015 | Chuang .................. G01N 11/10 702/50 |
| 2015/0258780 A1* | 9/2015 | Hayashi ............... B41J 2/04581 347/6 |

FOREIGN PATENT DOCUMENTS

| | | |
|---|---|---|
| JP | H04-032745 A | 2/1992 |
| JP | 10-197329 A | 7/1998 |
| JP | 11153582 A | 6/1999 |
| JP | 2001-059806 A | 3/2001 |
| JP | 2011-059104 A | 3/2011 |
| KR | 10-2011-0079919 A | 7/2011 |
| WO | WO 2011/065177 A1 | 6/2011 |

OTHER PUBLICATIONS

Schonhorn, "Surface Tension-Viscosity Relationships for Liquids," Journal of Chemical and Engineering Data, 12(4): 524-525, Oct. 1, 1967.

Tsukada et al., "A Theoretical and Experimental Study on the Oscillation of a Hanging Drop," Journal of Chemical Engineering of Japan, 20(1): 88-93, 1987.

Japanese Decision to Grant a Patent for Application No. 2016-569876, dated Aug. 21, 2018, 4 pages.

* cited by examiner

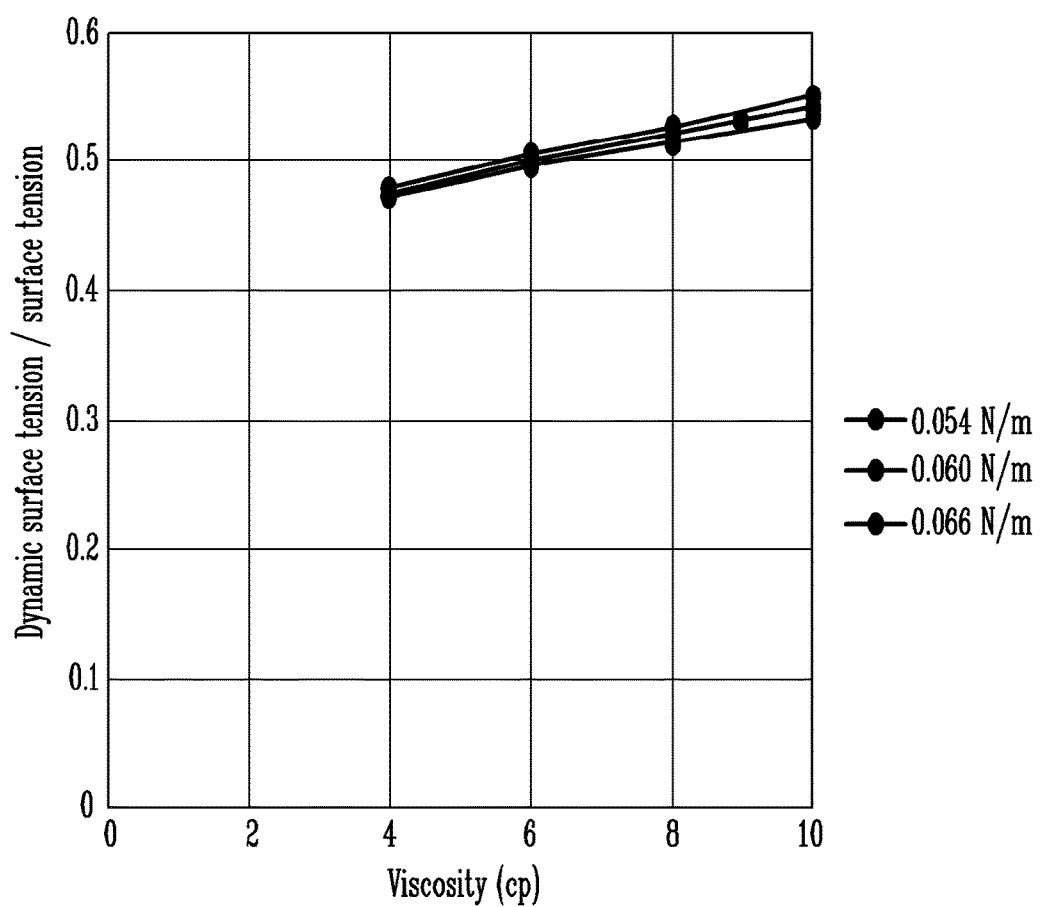

VISCOSITY MEASURING METHOD

This is the U.S. National Phase of International Patent Application No. PCT/KR2015/004889, Filed May 15, 2015, which claims priority to Korea Patent Application No. 10-2014-0064405, filed May 28, 2014, the disclosures of which are incorporated herein by reference in their entirety.

FIELD OF THE INVENTION

The present invention relates to a viscosity measuring method. More particularly, the present invention is directed to a viscosity measuring method comprising: (i) a step of acquiring an image of a droplet in a static state without vibration; (ii) a step of using a vibrator to vibrate the droplet, and acquiring an image of the droplet in a dynamic state in which the droplet is maximally extended in a horizontal direction or maximally extended in a vertical direction; (iii) a step of obtaining the static curvature change rate of the droplet interface and the dynamic curvature change rate of the droplet interface from the images acquired in step (i) and (ii); and (iv) a step of substituting the ratio of the static curvature change rate of the droplet interface to the dynamic curvature change rate of the droplet interface into an interaction equation adjusted for the vibrator, to obtain the viscosity of the droplet.

BACKGROUND OF THE INVENTION

Viscosity of a fluid is a measure of its resistance to flow. Namely, viscosity means internal friction of a fluid in motion. Mathematically, viscosity is expressed as the ratio of tangential friction per unit area to velocity gradient perpendicular to flow direction of a fluid.

A viscometer is an instrument that measures viscosity of a fluid. Currently, well-used viscometers are capillary viscometer, rotational viscometer, etc. Measuring principle and function of such viscometers are as follows.

The rotational viscometer is an instrument that measures viscosity of a fluid by measuring the resistance caused by fluid in motion to a cylinder or a disk. The rotational viscometer, though appropriate for measuring viscosity within intermediate shear rate range, is not appropriate for measuring viscosity within zero shear rate range.

The capillary viscometer is an instrument that measures viscosity of a fluid by measuring mass flow and falling pressure of a fluid in a steady flow state and then using Poiseuille's Law. However, in case of using capillary viscometer to measure the viscosity, capillary ought to be precisely calibrated because viscosity is proportional to biquadrate of capillary diameter.

More particularly, in case of using disposable capillary viscometer to measure the viscosity of blood, it is difficult to calibrate every disposable fluid tube accurately. Furthermore, capillary ought to be perfectly cleansed after the calibration. If a capillary is not calibrated, in fact, accuracy of the measured value of the blood viscosity cannot be guaranteed.

The mechanical methods for measuring viscosity by the above arts are difficult to be applied particularly in diagnosis instruments or examination instruments, due to excessive amount of fluid consumed and pollution.

In case of image-based viscosity measuring method, the method requires little amount of fluid, costs little, and is able of quick measurement, but is difficult to measure with accuracy. The reason is that, in case of measuring the viscosity using the natural frequency of a droplet, the natural frequency of the droplet is hardly affected by viscosity. Furthermore, in case of measuring the viscosity by using an amplitude of a droplet, it is difficult to measure with accuracy because the amplitude of the droplet is subtly affected by not only viscosity but also volume, surface tension and density of the droplet and amplitude of the droplet vibrator, and these diverse variables cannot be accurately calibrated.

The present inventor completed the present invention having found that the ratio of the dynamic curvature change rate of a vibrating droplet to the static curvature change rate of the droplet is only affected by the viscosity of a fluid.

DETAILED DESCRIPTION

Technical Problem

The purpose of the present invention is to provide a viscosity measuring method comprising: (i) a step of acquiring an image of a droplet in a static state without vibration; (ii) a step of using a vibrator to vibrate the droplet, and acquiring an image of the droplet in a dynamic state in which the droplet is maximally extended in a horizontal direction or maximally extended in a vertical direction; (iii) a step of obtaining the static curvature change rate of the droplet interface and the dynamic curvature change rate of the droplet interface from the images acquired in step (i) and (ii); and (iv) a step of substituting the ratio of the static curvature change rate of the droplet interface to the dynamic curvature change rate of the droplet interface, obtained by using the following equation (3), into an interaction equation adjusted for the vibrator, obtained by using the following equation (4), $$\frac{\sigma_d}{\sigma} = -\frac{\Delta \rho g}{\sigma} \frac{1}{(\partial \kappa / \partial z)_d} = \frac{(\partial \kappa / \partial z)_s}{(\partial \kappa / \partial z)_d} \qquad \text{Equation (3)}$$

$$\mu = f\left(\frac{(\partial \kappa / \partial z)_s}{(\partial \kappa / \partial z)_d}\right) \qquad \text{Equation (4)}$$

to obtain the viscosity of the droplet.

Solution to Problem

The present invention stated above may be achieved by providing a viscosity measuring method comprising: (i) a step of acquiring an image of a droplet in a static state without vibration; (ii) a step of using vibrator to vibrate the droplet, and acquiring an image of the droplet in a dynamic state in which the droplet is maximally extended in a horizontal direction or maximally extended in a vertical direction; (iii) a step of obtaining the static curvature change rate of the droplet interface and the dynamic curvature change rate of the droplet interface from the images acquired in step (i) and (ii); and (iv) a step of substituting the ratio of the static curvature change rate of the droplet interface to the dynamic curvature change rate of the droplet interface obtained by the following equation (3), into an interaction equation adjusted for the vibrator obtained by the following equation (4), $$\frac{\sigma_d}{\sigma} = -\frac{\Delta \rho g}{\sigma} \frac{1}{(\partial \kappa / \partial z)_d} = \frac{(\partial \kappa / \partial z)_s}{(\partial \kappa / \partial z)_d} \qquad \text{Equation (3)}$$

$$\mu = f\left(\frac{(\partial \kappa/\partial z)_s}{(\partial \kappa/\partial z)_d}\right) \quad \text{Equation (4)}$$

to obtain the viscosity of the droplet.

In the method of the present invention, the droplet may be hanging under a vibrator or placed on a vibrating plate. The droplet is vibrated by the vibrator or the vibrating plate, and it is filmed to obtain the image of the droplet in the state of maximal expansion in horizontal direction or maximal expansion in vertical direction. The droplet image, in a static state without vibration, may be obtained before or after obtaining the image in a dynamic state.

Hereafter, the droplet interface curvature change rate in a static state is obtained from the droplet image in a static state, and the droplet curvature change rate in a dynamic state is obtained by using all or one of the droplet images in the dynamic state.

Using the curvature change rate obtained in the above, the droplet curvature change rate in the static state and the droplet curvature change rate in the dynamic state is substituted into an interaction equation, previously obtained and adjusted for the vibrator, to obtain the viscosity of the droplet.

The method of the present invention may be applied to diverse liquids, in particular, body fluid. More specifically, the body fluid may be blood, urine, etc.

Advantageous Effects of the Invention

According to the method of the present invention, the viscosity of a fluid may be measured very easily, precisely and quickly. More particularly, the method of the present invention may be usefully applicable to the field of examination and diagnosis, such as viscosity measurement of blood.

BRIEF DESCRIPTION OF THE DRAWINGS

FIG. 5 shows the change in the ratio of the dynamic curvature change rate of the droplet to the static curvature change rate of the droplet at its natural frequency according to surface tension of the droplet.

BEST MODE FOR CARRYING OUT THE INVENTION

Figure 1:
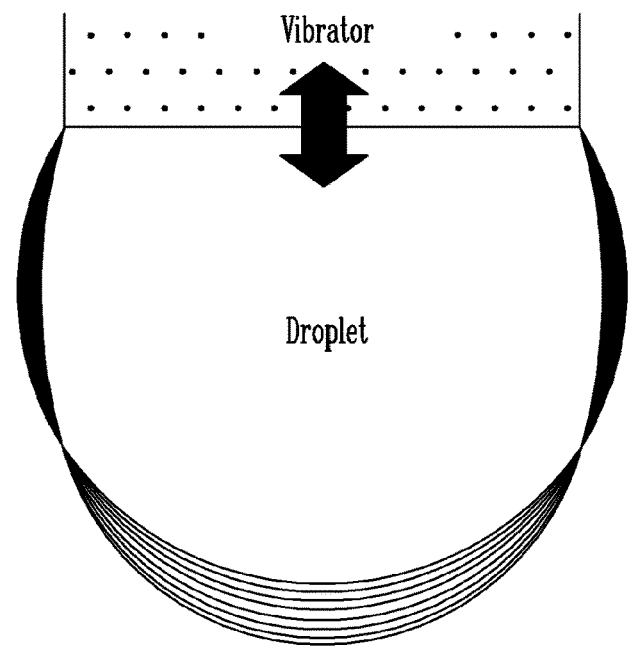
FIG. 1 shows a vibrating droplet according to one of the exemplary embodiment of the present invention, to measure the viscosity.

Hereinbelow, the present invention will be described in greater detail with reference to the following drawings. However, description of the following drawings is intended to specially focus on the description of the specific exemplary embodiment of the present invention. It is not intended to limit or to limit the interpretation of the scope of a right of the present invention by what is written in the description of the following drawings.

The viscosity measuring method of the present invention, using the ratio of the dynamic curvature change rate of the droplet to the static curvature change rate of the droplet, analyzes interface shape of the droplet to obtain necessary information for the viscosity measurement.

The droplet interface shape in a static state is formed with balance between capillary force ($\sigma\kappa$) occurring due to surface tension ($\sigma$) and curvature of interface ($\kappa$), and hydraulic head ($\Delta\rho gz$) in proportion to height (z) generated by density contrast ($\Delta\rho$) between the droplet and the open air. This is described as a static Young-Laplace equation of the following equation (1).

$$\left(\frac{\partial \kappa}{\partial z}\right)_s = -\frac{\Delta\rho g}{\sigma} \quad \text{Equation (1)}$$

In the above equation (1), $$\frac{\partial \kappa}{\partial z}$$

is interface curvature change rate in the direction of height, and the subscript "s" indicates the static state. The curvature change rate is calculated from the interface shape obtained by filming of a droplet in the static state, and is substituted into the equation (1) to obtain the ratio of the surface tension to the density contrast. Methods of obtaining the curvature change rate from the interface shape include diverse methods such as numerical analysis method, perturbation method or method of using width and height of the droplet, etc.

According to the viscosity measuring method of the present invention, the droplet vibrated at its natural frequency is snapshotted, and the interface shape of the droplet is analyzed. The droplet may be in a form of pendent drop, hanging under a vibrating device, or in a form of sessile drop, placed on a vibrating plate. As the droplet vibrates, it repeats a process of prolate expansion followed by oblate expansion. At this moment, the interface curvature change rate of the droplet in the dynamic state can be obtained by filming the distorted droplet to conduct the interface shape analysis. New parameter ($\sigma_d$) of identical unit to the surface tension can be obtained by substituting the above droplet curvature change rate in the dynamic state into the following equation (2).

$$\sigma_d = -\Delta\rho g \frac{1}{(\partial \kappa/\partial z)_d} \quad \text{Equation (2)}$$

In the above equation (2), subscript "d" indicates the dynamic state. New parameter obtained in this method does not indicate an already-established physical property, but it is defined as the dynamic curvature tension in the present description.

Whilst the dynamic curvature tension subtly changes according to the droplet viscosity, it is hardly affected by the volume change of the used droplet. Furthermore, the dynamic curvature tension changes when the surface tension of the used droplet changes, but the ratio of the dynamic curvature tension to the actual surface tension in static state ($\sigma_d/\sigma$), defined in the following equation (3), hardly changes, while only affected by viscosity. As in the following equation (3), this value becomes equal to the ratio of the dynamic curvature change rate to the static curvature change rate, thus becoming a dimensionless number unrelated to viscosity, surface tension and gravity of the fluid.

$$\frac{\sigma_d}{\sigma} = -\frac{\Delta \rho g}{\sigma} \frac{1}{(\partial \kappa/\partial z)_d} = \frac{(\partial \kappa/\partial z)_s}{(\partial \kappa/\partial z)_d} \quad \text{Equation (3)}$$

Therefore, by using the viscosity measuring method of the present invention, the equation is revised for the amplitude of the vibrator used in the measurement, and the ratio of the curvature change rate according to viscosity, $$\frac{(\partial \kappa/\partial z)_s}{(\partial \kappa/\partial z)_d}$$

is measured and saved as an adjusted interaction equation of the following equation (4).

$$\mu = f\left(\frac{(\partial \kappa/\partial z)_s}{(\partial \kappa/\partial z)_d}\right) \quad \text{Equation (4)}$$

Furthermore, when measuring the viscosity of a new fluid, the viscosity may be accurately measured, independent of the volume change and the surface tension change of the used droplet by using the equation (4) which is an interaction equation adjusted for the vibrator in which $(\partial \kappa/\partial z)_s$ is obtained by analyzing the interface shape of the droplet in a static state and $(\partial \kappa/\partial z)_d$ is obtained by analyzing the interface shape of the droplet in a vibrating state.

In the method of the present invention, parametric studies on each parameter were performed to examine whether the relation between the ratio of the curvature change rate and the viscosity is independent from the volume change and the surface tension change of the used droplet.

However, because it is in fact nearly impossible to independently modify the factors affecting the vibration of the droplet, including the viscosity, the surface tension and the volume, etc., by experiment, numerical analysis was used to simulate the vibration of the droplet and to independently modify each factor to examine the effects.

First, in order to examine the effect of the volume, the volume of the fluid of surface tension of 0.06 N/m was increased from 9 μl to 10 μl and to 11 μl, and the results of vibration were compared.

Figure 2:
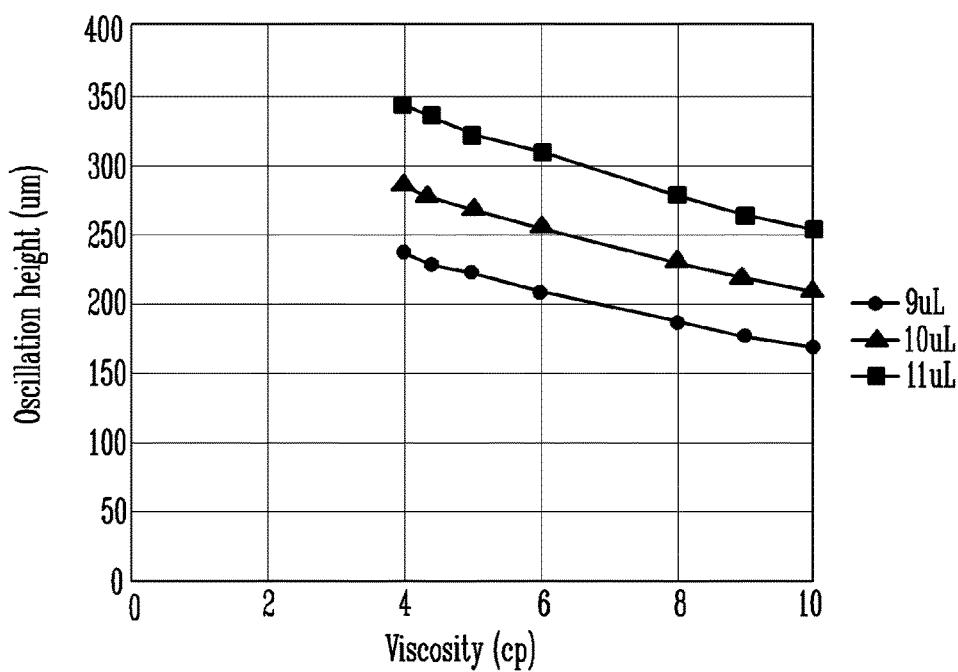
FIG. 2 shows an amplitude change of the droplet at its natural frequency according to volume of the droplet.

As shown in FIG. 1, examination of the droplet amplitude identifies that the droplet amplitude changes according to the viscosity as well as the volume of the used droplet very subtly. On the other hand, as shown in FIG. 2, the dynamic curvature tension changes subtly according to the viscosity but not to the surface tension.

Next, in order to examine the effect of the surface tension, the surface tension of the droplet having a volume of 10 μl was modified from 0.054 N/m to 0.06 N/m and to 0.066 N/m, and the results of vibration were compared.

Figure 3:
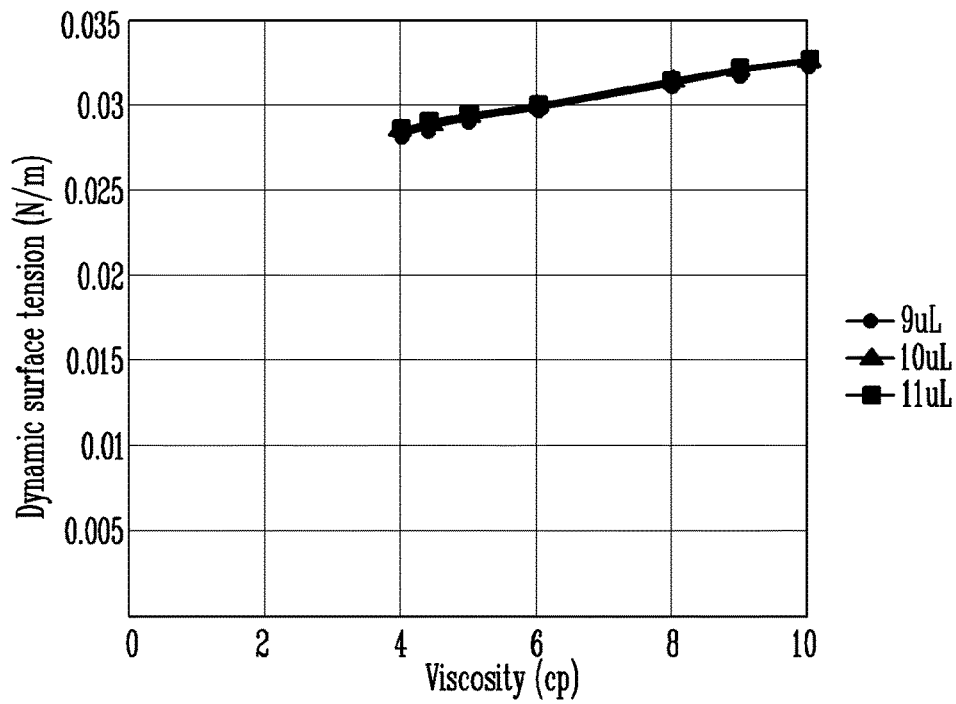
FIG. 3 shows the dynamic curvature change rate of the droplet at its natural frequency according to volume of the droplet.
Figure 4:
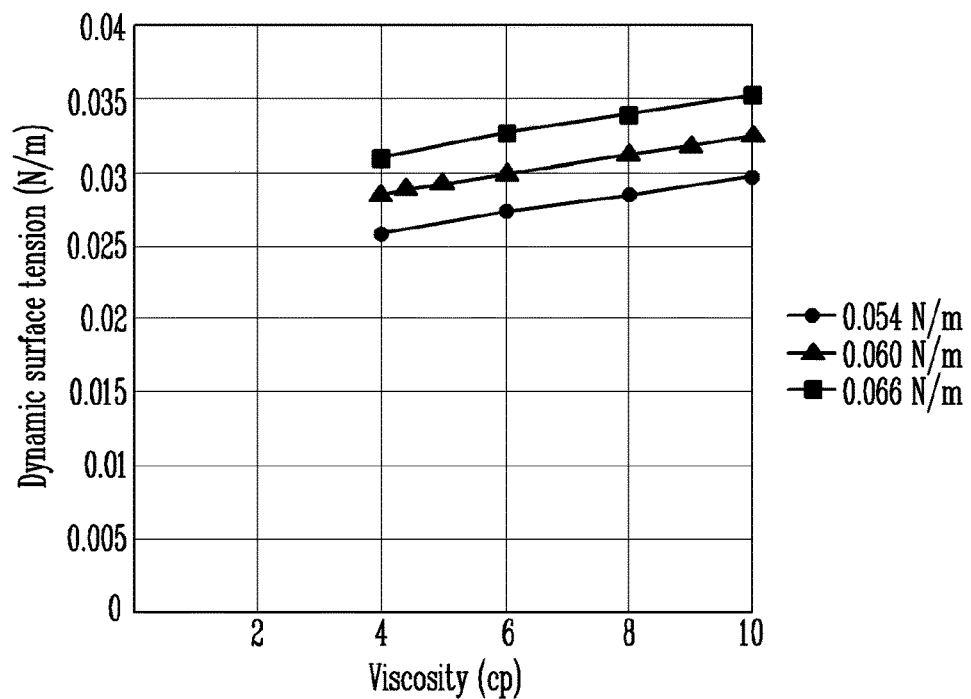
FIG. 4 shows the change of dynamic curvature change rate of the droplet at its natural frequency according to surface tension of the droplet.

As shown in FIG. 3, the dynamic curvature tension changes subtly according to the surface tension. On the other hand, as shown in FIG. 4, the ratio of the dynamic curvature tension to the surface tension changes subtly according to the viscosity, but not greatly to the surface tension.

The invention claimed is:

1. A viscosity measuring method comprising:
    (i) a step of acquiring an image of a droplet in a static state without vibration;
    (ii) a step of using a vibrator to vibrate the droplet, and acquiring an image of the droplet in a dynamic state in which the droplet is maximally extended in a horizontal direction or maximally extended in a vertical direction;
    (iii) a step of obtaining the static curvature change rate of the droplet interface and the dynamic curvature change rate of the droplet interface from the images acquired in step (i) and (ii); and
    (iv) a step of substituting the ratio of the static curvature change rate of the droplet interface to the dynamic curvature change rate of the droplet interface obtained by the following equation (3), into an interaction equation, adjusted for the vibrator, obtained by the following equation (4), to obtain the viscosity of the droplet $$\frac{\sigma_d}{\sigma} = -\frac{\Delta \rho g}{\sigma} \frac{1}{(\partial \kappa/\partial z)_d} = \frac{(\partial \kappa/\partial z)_s}{(\partial \kappa/\partial z)_d} \quad \text{Equation (3)}$$

$$\mu = f\left(\frac{(\partial \kappa/\partial z)_s}{(\partial \kappa/\partial z)_d}\right). \quad \text{Equation (4)}$$

2. The viscosity measuring method of claim 1, in which the droplet is dangling under the vibrator or placed on a vibrating plate.

3. The viscosity measuring method of claim 1, in which the droplet is a body fluid.

4. The viscosity measuring method of claim 3, in which the body fluid is blood.

* * * * *